United States Patent [19]

Tagamolila

[11] Patent Number: 5,043,500

[45] Date of Patent: Aug. 27, 1991

[54] USE OF STEAM EDUCTOR TO SUPPLY OXYGEN FOR OXIDATIVE REHEATING IN DEHYDROGENATION OF $C_3+$ HYDROCARBONS

[75] Inventor: Constante P. Tagamolila, Arlington Heights, Ill.

[73] Assignee: UOP, Des Plaines, Ill.

[21] Appl. No.: 453,899

[22] Filed: Dec. 20, 1989

[51] Int. Cl.⁵ .......................................... C07C 5/327
[52] U.S. Cl. ..................... 585/319; 585/324; 585/443; 585/444; 585/621; 585/624; 585/658
[58] Field of Search ............... 585/319, 324, 443, 444, 585/621, 624, 658

[56] References Cited

U.S. PATENT DOCUMENTS

| | | | |
|---|---|---|---|
| 3,409,689 | 11/1968 | Ward | 260/669 |
| 3,437,703 | 4/1969 | Reitmeier et al. | 260/669 |
| 3,502,737 | 3/1970 | Ghublikian | 260/669 |
| 3,515,766 | 6/1970 | Root et al. | 260/669 |
| 3,855,330 | 12/1974 | Mendelsohn et al. | 260/669 R |
| 4,150,064 | 4/1979 | Miklas | 585/625 |
| 4,152,393 | 5/1979 | Callahan | 585/444 |
| 4,778,941 | 10/1988 | Tagamolila | 585/319 |

Primary Examiner—Patrick P. Garvin
Assistant Examiner—G. Fourson
Attorney, Agent, or Firm—Thomas K. McBride; John G Tolomei

[57] ABSTRACT

A dehydrogenation process, where a hydrocarbon feed is dehydrogenated in a dehydrogenation zone and then oxidatively reheated by the combustion of hydrogen in an oxidation zone containing an oxidation catalyst, is improved by using a stream of dilution steam as an educing fluid to draw oxygen into contact with the effluent from the dehydrogenation zone ahead of the oxidation zone. A stream of dilution steam is often combined with the dehydrogenation zone effluent in order to control the oxygen concentration ahead of the oxidation zone and to lower the hydrogen partial pressure. Educing the oxygen-containing gas for the oxidation zone into the process by using the dilution steam an an educing fluid eliminates the need for compression of the oxygen-containing gas and prevents oxygen from contacting the dehydrogenation zone effluent before the dilution steam is admixed therewith. This process is particularly beneficial in the dehydrogenation of ethylbenzene to produce styrene.

10 Claims, 1 Drawing Sheet

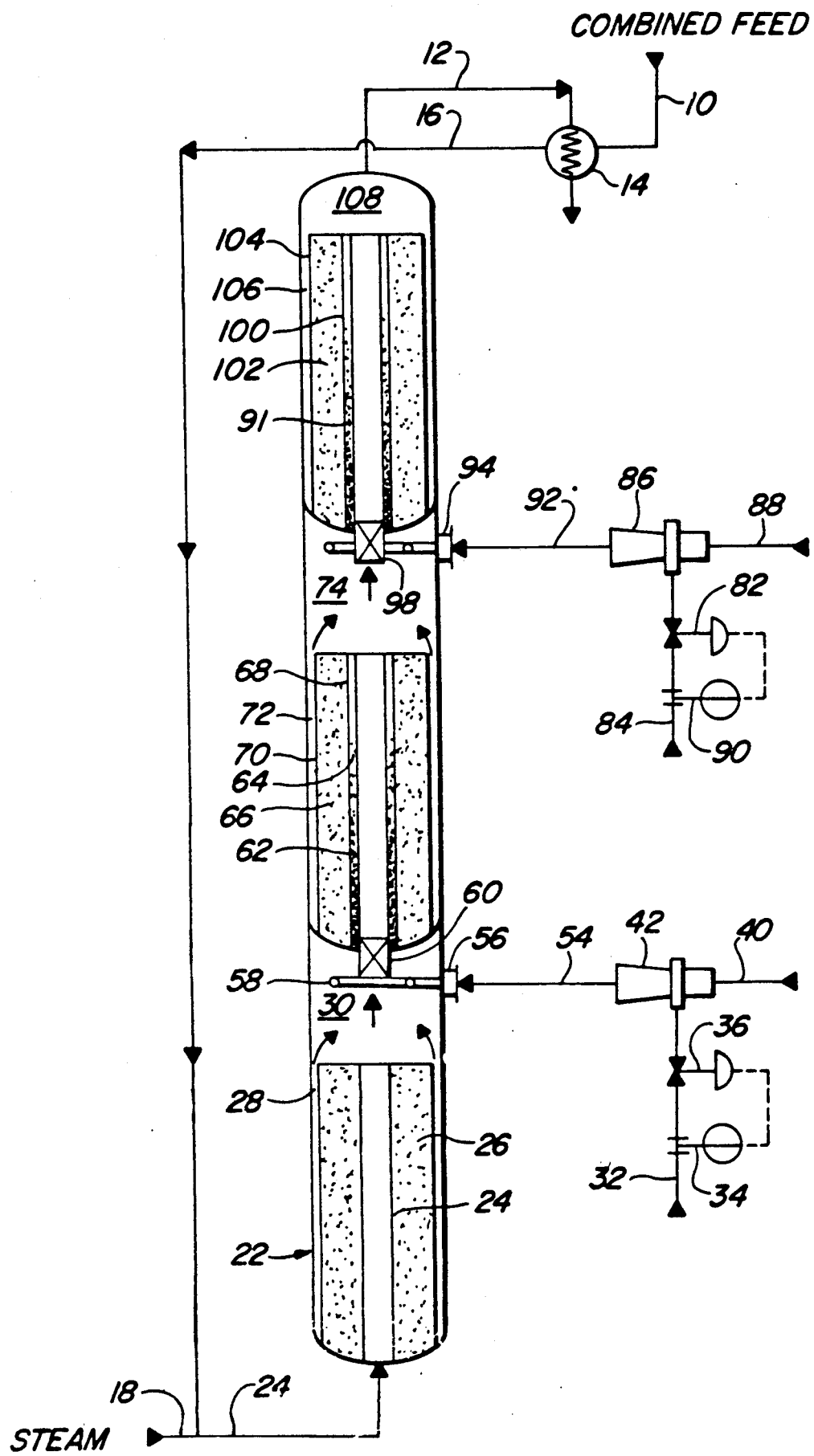

USE OF STEAM EDUCTOR TO SUPPLY OXYGEN FOR OXIDATIVE REHEATING IN DEHYDROGENATION OF $C_3+$ HYDROCARBONS

FIELD OF THE INVENTION

The invention relates to the general area of hydrocarbon conversion processes. In particular, the invention relates to a process for the catalytic dehydrogenation of hydrocarbons. The preferred use of the subject method is in the dehydrogenation of alkylaromatic hydrocarbons such as the conversion of ethylbenzene to styrene. The invention is specifically related to the mixing of steam and an oxygen-containing gas and the addition of the mixture to a bed of a selective hydrogen oxidation catalyst used in a dehydrogenation zone.

INFORMATION DISCLOSURE

The dehydrogenation of hydrocarbons is well described in the prior art, with both acyclic and aromatic hydrocarbons being thereby converted to the corresponding less saturated products. For instance, dehydrogenation is performed commercially for the production of styrene from ethylbenzene to fulfill the sizable demand for this polymer precursor. U.S. Pat. Nos. 3,515,766 (Root et al.) and 3,409,689 (Ward) are pertinent for their showing of typical prior art catalytic steam dehydrogenation processes for alkylaromatics including ethylbenzene. These references describe the admixture of superheated steam into the feed hydrocarbon and the admixture of additional amounts of superheated steam with the reactants between sequential beds of dehydrogenation catalyst to reheat the reactants.

It is also known in the prior art to pass oxygen into a dehydrogenation zone for the purpose of reacting the oxygen with hydrogen released during the dehydrogenation reaction to thereby liberate heat and to consume hydrogen. The processes known to employ this technique utilize a hydrogen oxidation catalyst in an attempt to selectively oxidize the hydrogen rather than feed or product hydrocarbons also present in the dehydrogenation zone. For instance, U.S. Pat. No. 3,437,703 (Reitmeier et al.) discloses a dehydrogenation process which may utilize either a "homogeneous catalyst system" in which oxidation and dehydrogenation catalysts are admixed or a layered system or individual catalyst beds referred to as a "multibed" system. Similarly, U.S. Pat. No. 3,855,330 (Mendelsohn et al.) discloses a dehydrogenation process using sequential beds of dehydrogenation catalyst and oxidation catalyst. It is taught in this reference that it is desirable that oxygen does not come into contact with the dehydrogenation catalysts, and that the major part or all of the added oxygen should be consumed within the bed of oxidation catalyst.

U.S. Pat. No. 3,502,737 (Ghublikian) presents a process for the dehydrogenation of ethylbenzene which indicates catalyst activity and stability are maintained by the careful control of the amount of oxygen which is present and by a reduction in the steam which is used in the reaction zone. An oxygen-containing gas such as air is supplied both initially and at interstage points in a carefully controlled manner. It is believed that the teaching of this reference is limited to the use of a catalyst system comprising a physical admixture of the hydrogen oxidation catalyst and the dehydrogenation catalyst, with the presence of oxygen being credited with assisting in the prevention of carbon deposits on the surface of catalytically active sites of the dehydrogenation catalyst.

It is also known to increase the amount of hydrogen consumed in a separate bed of oxidation catalyst by cooling the reactant stream and thereby increasing the amount of heat which must be generated in the oxidation catalyst bed to heat the reactant stream. U.S. Pat. No. 4,778,941 teaches the use of an eductor to withdraw a portion of a dehydrogenation effluent from the reactor, cool it, and return it to the reactor. The oxygen-containing gas stream that provides oxygen for the oxidation section is used as the educing fluid. The oxygen-containing gas stream is compressed to provide the gas velocity for operation of the eductor.

When oxygen is added to the hydrocarbons between dehydrogenation and oxidation reaction zones, the proportions of oxygen and hydrocarbons must be outside of the flammability range for these gases. Careful mixing and control of the oxygen addition is practiced to avoid flammable proportions of oxygen and hydrocarbons. In addition, to further reduce the overall concentration of oxygen and hydrocarbon in the reaction section and avoid the flammability range for these reactants, steam is often added with an oxygen gas to dilute the relative proportion of oxygen and hydrogen in the reactor. To be effective, the addition of dilution steam also requires careful mixing of the steam and oxygen-containing gas before it enters the reactor and is further mixed with the hydrocarbons. Where dilution steam is mixed with the oxygen-containing gas to avoid flammability conditions, it is important to prevent oxygen from entering the process without the addition of steam.

BRIEF SUMMARY OF THE INVENTION

The subject invention provides an improved method of introducing an oxygen-containing gas and a dilution steam stream into an oxidatively reheated dehydrogenation zone. The invention uses a dilution gas stream as the educing fluid in an eductor to pull an oxygen-containing gas into admixture therewith and then transfers the mixture into contact with a dehydrogenation zone effluent that flows from a dehydrogenation zone into an oxidated reheat zone for a dehydrogenation process. Using the eductor to draw the oxygen-containing gas into the process, eliminates the need for a compressor to compress the oxygen-containing gas. Since the steam for addition to the process is already available at at least moderate pressure, there is no need for any additional compression to add the oxygen-containing gas to the process. In addition to the savings on compression, additional safeguards are provided in the process by this method. Use of the steam as the educing fluid will prevent any addition of oxygen to the process in the case where the flow of dilution steam is lost for any reason. Therefore, the arrangement of this invention provides a process that is more energy efficient and safer to operate.

In one embodiment this invention is characterized as a dehydrogenation process which comprises the steps of passing a feedstream comprising a $C_3$-plus dehydrogenatable hydrocarbon into a reaction zone having a dehydrogenation zone and through a first bed of dehydrogenation catalyst maintained at dehydrogenation conditions, and producing a dehydrogenation zone effluent stream comprising hydrogen, a portion of the $C_3$-plus feed hydrocarbon, and a $C_3$-plus product hydrocarbon. In normal practice, the dehydrogenation zone effluent and an oxygen-containing gas stream are admixed and passed into a separate bed of selected hydrogenation oxidation catalysts maintained at oxidation promoting conditions in order to produce an oxidation zone effluent stream which is passed into a second bed of dehydrogenation catalyst. In this embodiment, the process is improved by injecting steam into contact with the dehydrogenation zone effluent and using the steam to educe the oxygen-containing gas stream first into admixture with the steam, thereby simultaneously mixing the steam with the oxygen-containing gas and thereafter combining the steam and the oxygen-containing gas mixture with the dehydrogenation zone effluent.

Additional embodiments and details of this invention are provided in the following detailed description of the invention.

BRIEF DESCRIPTION OF THE DRAWING

FIG. 1 is a schematic view of the process of this invention showing a section view of the reaction vessel and equipment for the addition of dilution steam and oxygen-containing gas to the reaction vessel.

DETAILED DESCRIPTION OF THE INVENTION

Processes for the dehydrogenation of aromatic hydrocarbons are in widespread commercial use. For instance, large quantities of styrene are produced by the dehydrogenation of ethylbenzene. The resultant styrene may be polymerized with itself or it may be copolymerized with butadiene, isoprene, acrylonitrile, etc. Other hydrocarbons which may be dehydrogenated in much the same manner include diethylbenzene, ethyl toluene, propylbenzene, and isopropylbenzene. The subject process can also be applied to the dehydrogenation of other types of hydrocarbons including relatively pure or mixed streams of $C_2$-$C_{16}$ paraffins. The process can therefore be applied to the dehydrogenation of propane, butanes, hexanes, or nonanes. However, since the great majority of the present commercial dehydrogenation processes are employed for the dehydrogenation of ethylbenzene, the following description of the subject invention will be presented primarily in terms of the dehydrogenation of ethylbenzene. This is not intended to exclude from the scope of the subject invention those alkylaromatic and acyclic hydrocarbons set out above or those having different ring structures including bicyclic compounds.

The dehydrogenation reaction is highly endothermic. Therefore, passing the reactants through a dehydrogenation catalyst bed results in a decrease in the reactant temperature. The endothermicity of the reaction is such that the temperature decrease removes the reactants from the desired temperature range. The reactants are actually cooled to such an extent that the desired reaction does not progress any further at a commercially feasible rate. The desired or commercially necessary per pass conversion therefore cannot be achieved by simply passing the reactants into contact with a single bed of dehydrogenation catalyst. For this reason, it has become standard commercial practice to in some manner perform interstage reheating. In interstage reheating, the reactant effluent of a first bed of catalyst is heated to the desired inlet temperature of a second downstream bed of catalyst. This reheating can be performed through direct heat exchange as by the admixture of high temperature steam into the reactant stream emerging from the first catalyst bed. This accomplishes the desired heating, but has a number of drawbacks including the utilities cost of producing the high temperature steam. It also increases the amount of steam which must be condensed to recover the product alkylaromatic hydrocarbons from the effluent stream and increases the total amount of material flowing through the reaction zone, thereby making it more difficult to maintain desired low pressures within the reaction zone.

Another method of interstage reheating comprises the use of indirect heat exchange. In this method, the effluent from a dehydrogenation zone is passed through a heat exchanger in which it is heated, and the reactants are then passed into the subsequent dehydrogenation zone. The high temperature fluid employed in this indirect heat exchange method may be high temperature steam, combustion gases, a high temperature process stream, or other readily available high temperature fluids. This method of interstage heating does not dilute the reactants but does impose some pressure drop in the system and can expose the reactants to undesirably high temperatures.

A third method of interstage heating is the oxidative reheat method. This is a newer method which it is believed has not been employed commercially. The driving force for employing the oxidative reheat method is the recognition that the combustion of the hydrogen generated in the dehydrogenation process performs two functions which are beneficial in the dehydrogenation process. First, the consumption of the hydrogen is beneficial in shifting the equilibrium of the dehydrogenation reaction to favor increased amounts of dehydrogenation. Second, the combustion of the hydrogen will release heat sufficient to reheat the reactants to the desired dehydrogenation conditions. The oxidation is preferably accomplished in the presence of a catalyst which selectively promotes the oxidation of hydrogen as compared to the destructive combustion or oxidation of the more valuable feed and product hydrocarbons. The selective combustion method of interstage reheating presents a more economical dehydrogenation process. Oxidative reheat to a significant extent is supplanting indirect heat exchange as a method of performing the required interstage heating.

Despite the advances which have been achieved in the arts of catalysis and hydrocarbon conversion, the ultimate conversion which can be achieved during a single passage through an overall dehydrogenation zone is limited to an amount less than total conversion. That is, it is impossible to achieve a 100% conversion of a feed hydrocarbon to a corresponding product dehydrogenated hydrocarbon. A basic limitation in the degree of conversion which may be achieved in any dehydrogenation processes is the equilibrium concentration of the various reactants at the temperatures employed. The effluent stream of a catalytic dehydrogenation zone will therefore comprise an admixture of the unreacted feed hydrocarbon and the product hydrocarbon and hydrogen. It is necessary to separate and recover the product hydrocarbon and to recycle the unconverted feed hydrocarbon. The greater the rate of conversion which is achieved in the dehydrogenation zone, the smaller the amount of unconverted material which must be recycled becomes. The separation of the product and unreacted hydrocarbons requires extensive capital equipment and consumes large amounts of utilities in the form of heat and electrical power. It is therefore desirable to increase the conversion which is achieved per pass in the dehydrogenation zone and to thereby decrease the amount of material which must be separated and recycled through the reactor. A higher per passage conversion will also allow a smaller reaction zone to be employed in the process with the associated reduction in the cost of the reactors, catalyst and utilities cost of operating the reaction zone. For these reasons, it is highly desirable to achieve increased rates of total conversion during the passage of the dehydrogenation zone feed stream through a multibed dehydrogenation reaction zone. Methods of cooling the dehydrogenation effluent to increase the consumption of hydrogen are taught in U.S. Pat. No. 4,599,471, the teachings of which are incorporated herein by reference.

In the oxidative reheat process, an oxygen-containing gas stream is admixed with the effluent of a preceding dehydrogenation zone and the resulting admixture is passed into a bed of selective hydrogen oxidation catalyst. To achieve the optimum levels of performance and safety in this process, it is necessary to closely control the rate at which oxygen is passed into the process in this manner. An insufficient amount of oxygen will result in a less than desired consumption of hydrogen and more importantly a less than desired reheating of the reactant stream. The result will be a decrease in the degree of dehydrogenation achieved during passage through the overall reaction zone. It is not normally desired to inject an excess amount of oxygen into any part of the oxidation zone above that required to perform the desired degree of hydrogen combustion. More specifically, in a normal operation which does not employ the subject process, no more than 60 mol. % of the net hydrogen produced in the preceding dehydrogenation zone need be combusted to achieve a desired degree of reheating.

The passage of an excess amount of oxygen into the dehydrogenation zone will also have detrimental effects upon the long term operation of the process. For instance, oxygen will normally serve to deactivate or poison some commercially employed dehydrogenation catalyst. It is therefore undesirable to have residual oxygen emerging from the oxidation catalyst bed and thereupon contacting dehydrogenation catalyst. The presence of oxygen is also not normally desired in vessels containing hydrocarbons as the oxygen may react with the hydrocarbons to form various undesired oxygenated compounds. Lastly, operation of the dehydrogenation zone in a manner which does not result in the total consumption of the oxygen is also undesirable because of the obvious flammable or explosive nature of oxygen-hydrocarbon mixtures. The explosive nature of these mixtures can, however, be essentially negated by properly operating the process to avoid the presence of mixtures being within the explosive range, as through the use of intentionally low oxygen addition rates, and the presence of a sufficient amount of solid material to act as an explosion suppression means.

It is also possible to control the relative hydrocarbon to oxygen concentrations by the use of suitable diluents. Low pressure steam is typically added to the oxygen-containing gas stream to maintain an oxygen concentration that is below the region of flammability for hydrocarbon and oxygen mixtures. In addition, the low pressure steam also serves as direct heat exchange medium for cooling of the oxygen-containing gas and effluent mixture. Although the added steam must be eventually removed from the recovered product streams, its addition provides favorable reductions in partial pressures.

In a broad sense, the feed to the dehydrogenation zone may consist of any dehydrogenatable $C_3$-plus hydrocarbon. Preferably, the process dehydrogenates a feed stream of ethylbenzene to obtain styrene. The process may also be used to dehydrogenate feedstreams of acyclic $C_3$–$C_8$ paraffins into their corresponding olefins. Other aromatic feed streams may also be charged to the dehydrogenation zone such as ethyltoluene in order to produce paramethylstyrene by dehydrogenation.

The alkylaromatic hydrocarbon to be dehydrogenated is preferably admixed with superheated steam to counteract the temperature lowering effect of the endothermic dehydrogenation reaction. The presence of steam has also been described as benefiting the stability of the dehydrogenation catalyst by preventing the accumulation of carbon deposits. Preferably, the steam is admixed with the other components of the feed stream in a weight ratio of steam to feed hydrocarbon of about 0.5 to about 1.7. Other quantities of steam may be added after one or more subsequent beds if desired. However, the weight ratio of steam to product hydrocarbon in the dehydrogenation zone effluent stream should be less than about 3 and preferably less than 2.

FIG. 1 illustrates the introduction of the feed and steam into a process for the dehydrogenation of ethylbenzene. In this process, a feed stream comprising relatively high purity ethylbenzene and lower temperature steam carried by a line 10 is heat exchanged against a hereinafter described effluent stream 12 in a heat exchanger 14. The heated feed stream is carried by a line 16, admixed with high temperature superheated steam from a line 18, and passed into a reaction vessel 20 having a dehydrogenation zone 22 by a line 24. The feed admixture enters a centerpipe 24 that radially distributes the mixture into a first bed of dehydrogenation catalyst 26 in which a portion of the ethylbenzene is dehydrogenated to produce styrene and hydrogen. The endothermic dehydrogenation reaction results in a reduction in temperature of the reactant stream as it passes through the dehydrogenation catalyst bed 26. The effluent stream of the catalyst bed 26 enters an annular volume 28 that collects the effluent and openly communicates it with a cylindrical void volume 30.

A line 40 carries steam to an eductor 42. The steam is preferably low pressure steam having a pressure of between 10 and 50 psig. An oxygen-containing gas, in this case air, is drawn from a line 32 through the eductor by the steam which serves as an educting fluid. The oxygen-containing gas is not limited to air but may be any oxygen-containing gas stream such as oxygen-enriched air, relatively pure oxygen streams, or any of the above diluted with inert vapors such as steam and $N_2$. The eductor is designed to provide good mixing and to simultaneously draw the oxygen-containing gas into admixture therewith. Contact of the steam and the oxygen-containing gas stream in the eductor thoroughly mixes these two streams. The eductor and associated piping are usually designed to draw in a quantity of oxygen equal to at least 5.0 wt. % of the effluent leaving the dehydrogenation zone using a quantity of steam that is usually equal to between 5 and 15 wt. % of the dehydrogenation zone effluent. Therefore the ratio of steam to oxygen containing gas entering the eductor is usually in a ratio of 1:1 to 3:1. The mixing of the oxygen containing gas stream and the dehydrogenation zone effluent will usually produce an oxygen concentration in the feed to the oxidation zone of 1.0 to 2.0 wt. %. Combining the effluent with the above proportions of steam and oxygen will avoid flammable proportions of the hydrocarbon and oxygen in the resulting mixture. Further details on the operation of eductors can be obtained from the *Chemical Engineers Handbook* published by McGraw-Hill Book Co. The amount of air withdrawn by the eductor is regulated by flow meter 34 and a control valve 36 which is adjusted in response to a signal from the control valve.

A line 54 carries the mixture of steam, air and effluent from the eductor to nozzles 56 where it reenters chamber 30 and is redistributed in chamber 30 by a distributor 58 having a location downstream of the point of effluent withdrawal. The admixture of steam and oxygen passes through a static mixer 60 along with the hydrogenation zone effluent to make sure that the reactants are well mixed. The larger bulk of the diluted $O_2$-containing vapor mixture improves the efficiency of component mixing in comparison to the mixing that is obtained when the oxygen stream enters the oxidation section without dilution steam. From mixer 60, the reactants enter a centerpipe 62 that distributes them into an annular bed 64 of oxidation catalyst. This catalyst promotes the selective combustion or oxidation of the hydrogen released in the bed of dehydrogenation catalyst to thereby consume the hydrogen and release heat. By controlling the amount of oxygen which is added through line 32, the extent to which the total amount of available hydrogen is combusted within bed 64 may also be controlled. These control parameters are preferably set on the basis of a temperature measurement taken at the outlet of the bed of oxidation catalyst. The control valve 36 may also be employed to regulate the outlet temperature of the oxidation catalyst bed effluent stream, which is the temperature of the reactants being charged to a second bed 66 of dehydrogenation catalyst. The rate of oxygen addition through line 58 is therefore preferably controlled on the basis of the preferred inlet temperature to the annular catalyst bed 66. As the reactants enter and flow through the dehydrogenation catalyst of bed 66, an additional amount of ethylbenzene is converted to styrene and an additional amount of hydrogen is produced. The reactants are also cooled by the endothermic dehydrogenation reaction.

Catalyst beds 64 and 66 are both annularly arranged. Catalyst bed 64 occupies an inner annular area defined by centerpipe 62 and an intermediate screen 68. Screen 68 separates the oxidation catalyst of bed 64 from the dehydrogenation catalyst of bed 66. Dehydrogenation catalyst bed 66 occupies an outer annular area defined by intermediate screen 68 on the inside and an outer screen 70 on the outside. The construction of the beds using perforated centerpipe 62 and screen sections 68 and 70 allows the reactants to flow serially through the oxidation and dehydrogenation catalysts and collect in an annular space 72 which communicates the effluent to another cylindrical void volume 74.

In substantially the same manner as described in relation to volume 30, a suction line 84 transports air into an eductor 86 wherein the effluent is thoroughly mixed with steam carried by line 88. The steam and air mixture are transferred back to the reactor vessel by a line 92. The rate of flow of the air through line 84 is again controlled, on the basis at least one temperature measurement including a temperature taken at or near the point of reactant exit from the next bed 91, using a flow meter 90, and a control valve 82. The mixture of line 92 reenters volume 74 through a nozzle 94 and a distributor 96.

The mixture of reactants entering through distributor 96 are again passed through a mixing device 98, to ensure thorough mixing before entering a centerpipe 100. From centerpipe 100, the reactant mixture enters and passes through the annular bed of oxidation catalyst 91 wherein it is heated by the combustion of hydrogen. The reactants are thereby heated to the desired inlet temperature of the annular bed 102 of dehydrogenation catalyst such that the additional desired amount of dehydrogenation occurs within this catalyst bed as the reactants pass outward. The reactants finally emerge from the outer surface of a cylindrical screen 104 located about the periphery of the catalyst bed 102 into an annular space 106 which is in open communication with a collection chamber 108 at the top of the reaction vessel 20 and are withdrawn through line 12 and pass from exchanger 14 to appropriate product recovery facilities such as described below. The effluent stream carried by line 12 will comprise an admixture of the residual unconverted ethylbenzene, hydrogen, steam from lines 18 and 44, steam which is formed within the dehydrogenation zone by the combustion of hydrogen, and reaction by-products including a small amount of light ends material, toluene, and benzene.

This presentation of one embodiment of the invention has been simplified by not including a description of those pieces of commonly used process equipment, such as other control systems, pumps, heat exchangers, etc. which are employed in the operation of the process but are not necessary for a description of the operation or construction of the subject invention. This presentation of certain embodiments of the invention is not intended to preclude from the scope of the invention those other embodiments set out herein or which are the result of normal and expected modification and variation to those embodiments.

The overall structure of the dehydrogenation zone is also subject to extensive variation. For instance, it could be a perforated toroidal chamber or a complex grid of piping having a circular or branching structure could be employed for the distribution of the oxygen-containing gas stream within the void volume 30 instead of the ring conduit having a multiplicity of outlet nozzles as shown in the drawing. The structure of the dehydrogenation zone ay also be varied by changing the type of catalyst bed which is employed. For instance, radial flow through annular catalyst beds depicted in the drawing may be replaced with vertical flow through cylindrical catalyst beds. It is to be noted that with a radial flow embodiment of the invention, the beds of dehydrogenation catalyst and oxidation catalyst need not be concentrically located at the same elevation within the vessel. It is also possible to locate either the oxidation catalyst or the dehydrogenation catalyst in the outer bed of a radial flow arrangement by changing the direction of gas flow through cylindrical centerpipe regions and annular gas collection and distribution void volumes located between the outer surface of the catalyst beds and the inner wall of the vessel. Variation is also possible in the number of beds of catalyst which may be employed within the dehydrogenation process. For instance, the dehydrogenation process could employ two separate beds of dehydrogenation catalyst and one bed of oxidation catalyst, or four beds of dehydrogenation catalyst and three beds of oxidation catalyst may be employed. A separate oxygen-containing gas stream would be used to educe gas flow immediately upstream of each bed of oxidation catalyst. The total amount of dehydrogenation catalyst employed in the process may be divided into ten or more separate beds, but the dehydrogenation zone preferably comprises two or three catalyst beds with means for the intermediate addition and admixture of any added steam and the oxygen supply stream. Suitable systems for this may be patterned after those presented in U.S. Pat. Nos. 3,498,755; 3,515,763; and 3,751,232. The catalyst beds may be contained in separate reaction vessels or they may be enclosed within a larger overall vessel or structure. The use of radial flow annular catalyst beds in a stacked configuration in a single overall vessel is preferred although the invention can be used with vertical flow in cylindrical beds.

Dehydrogenation catalysts generally consist of one or more metallic components selected from Groups VI and VIII of the Periodic Table. One typical catalyst for the dehydrogenation of alkylaromatics comprises 85% by weight ferric oxide, 2% chromia, 12% potassium hydroxide, and 1% sodium hydroxide. A second dehydrogenation catalyst, which is used commercially, consists of 87–90% ferric oxide, 2–3% chromium oxide, and from 8–10% potassium oxide. A third typical catalyst comprises 90% by weight iron oxide, 4% chromia, and 6% potassium carbonate. Methods for preparing suitable catalysts are well known in the art. This is demonstrated by the teachings of U.S. Pat. No. 3,387,053 which describes the manufacture of a catalytic composite of at least 35 wt. % iron oxide as an active catalytic agent, from about 1–8 wt. % zinc or copper oxide, about 0.5–50 wt. % of an alkali promoter, and from about 1–5 wt. % chromic oxide as a stabilizer and a binding agent. U.S. Pat. No. 4,467,046 also describes a catalyst for the dehydrogenation of ethylbenzene in the presence of steam. This catalyst contains 15 to 30 wt. % potassium oxide, 2 to 8% cerium oxide, 1.5 to 6% molybdenum oxide, 1 to 4% calcium carbonate, with the balance iron oxide.

Dehydrogenation conditions in general include a temperature of about 538°–750° C. and preferably about 565°–675° C. The temperature required for efficient operation of any specific dehydrogenation process will depend on the feed hydrocarbon and the activity of the catalyst employed. The pressure maintained within the dehydrogenation zone may range from about 100 to about 750 mm Hg, with a preferred range of pressures being from 250 to 700 mm Hg. The operating pressure within the dehydrogenation zone is measured at the inlet, mid-section, and outlet of the zone to thereby provide an approximately average pressure. The combined feed stream is charged to the dehydrogenation zone at a liquid hourly space velocity, based on liquid hydrocarbon charge at 15° C., of about 0.1 to about 2.0 hr$^{-1}$, and preferably from 0.2 to 1.0 hr$^{-1}$.

The effluent stream removed from the overall dehydrogenation zone is normally heat exchanged for the purpose of lowering its temperature for the recovery of heat. As mentioned, the effluent stream may be heat exchanged against a stream of steam, a reactant stream of this or another process, or used as a heat source for fractionation, etc. Commercially, the effluent stream is often passed through several heat exchangers, thereby heating a number of different streams. This heat exchange is performed subject to the constraints set out above. The heat exchange should cool the dehydrogenation zone effluent stream sufficiently to effect the condensation of at least 95 mol. % of the feed and product $C_6$-plus hydrocarbons and also at least 95 mol. % of the water vapor. The use of a partial quench to accomplish this condensation may or may not be employed. Essentially all of the styrene or other product hydrocarbon, most water, and other readily condensable compounds present in the effluent stream are thereby converted to liquids. This produces a mixed phase stream which is passed into a phase separation vessel. This procedure allows the facile crude separation by decantation of the hydrocarbons from the water and non-condensibles present in the effluent stream. The styrene present in the dehydrogenation zone effluent stream becomes part of a hydrocarbon stream which is withdrawn from the separation vessel and transferred to the proper separation facilities. Preferably, the styrene or other product hydrocarbon is recovered from the hydrocarbon stream by using one of the several fractionation systems known in the art. This fractionation will preferably yield a relatively pure stream of ethylbenzene, which is recycled, and an additional stream comprising benzene and toluene. These two aromatic hydrocarbons are by-products of the dehydrogenation reaction. They may be recycled in part as taught in U.S. Pat. No. 3,409,689 and British Pat. No. 1,238,602 or entirely rejected from the process. Styrene is recovered as a third stream, which is withdrawn from the process. If desired, methods other than fractionation may be used to recover the styrene. For instance, U.S. Pat. No. 3,784,620 teaches the separation of styrene and ethylbenzene through the use of a polyamide permeation membrane such as nylon-6 and nylon 6,10. U.S. Pat. No. 3,513,213 teaches a separatory method employing liquid-liquid extraction in which anhydrous silver fluoroborate is used as the solvent. Similar separatory methods utilizing cuprous fluoroborates and cuprous fluorophosphates are described in U.S. Pat. Nos. 3,517,079; 3,517,080; and 3,517,081.

The recovery of styrene through the use of fractionation is described in several references including U.S. Pat. No. 3,525,776. In this reference, the hydrocarbonaceous phase removed from the phase separation zone is passed into a first column referred to as a benzene-toluene column. This column is operated at a subatmospheric pressure to allow its operation at lower temperatures and hence reduce the rate of styrene polmerization. Various inhibitors such as elemental sulfur, 2,4-dinitrophenol, or a mixture of N-nitroso diphenylamine and a dinitroso-o-cresol are injected into the column for this same purpose. Sulfur can also be introduced into this column by returning at least a portion of the high molecular weight material separated from the bottoms stream of a styrene purification column. A more detailed description of this is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream preferably contains at least 95 mol. % benzene and toluene. The bottoms of the benzene-toluene column is passed into a second fractionation column from which ethylbenzene is removed as an overhead product and recycled. The bottoms stream of this column is then purified to obtain the styrene. Product recovery techniques directed to the recovery of vinyltoluene via fractionation and the use of chemical additives to inhibit polymerization are described in U.S. Pat. Nos. 4,417,085 and 4,492,675. The use of inhibitors and alternative fractionation techniques for readily polymerizable vinyl aromatic compounds is also described in U.S. Pat. No. 4,469,558.

The oxygen supply stream may be air or a gas having a higher oxygen content than air. It is preferred that the oxygen supply stream has a nitrogen content less than 10 mol. %. The preferred oxygen concentration in the oxygen supply stream is primarily a matter of economics and would be determined by a comparison of the advantage of having the higher oxygen concentration to the cost of obtaining the oxygen. The basic disadvantages of the presence of nitrogen are the dilution of the hydrogen-containing gas stream removed from the product separation vessel, and the fact that the nitrogen passes through the dehydrogenation zone, thereby increasing the pressure drop through the catalyst bed and the absolute pressure being maintained within the dehydrogenation zone. On the other hand, the presence of nitrogen favorably affects the equilibrium conversion level by acting as a diluent.

The oxidation catalyst employed in the subject process to promote the interstage hydrogen oxidation may be any commercially suitable catalyst which meets the required standards for stability and activity and which possesses high selectivity for the oxidation of hydrogen as compared with the oxidation of the feed to product hydrocarbon. That is, the oxidation catalyst must have a high selectivity for the oxidation of hydrogen with only small amounts of the feed or product hydrocarbon being oxidized. The oxidation catalyst will have a different composition from that of the dehydrogenation catalyst. The preferred oxidation catalyst comprises a Group VIII noble metal and a metal or metal cation which possesses a crystal ionic radius greater than 1.35 angstroms, with both of these materials being present in small amounts on a refractory solid support. The preferred Group VIII metals are platinum and palladium, but the use of ruthenium, rhodium, osmium, and iridium is also contemplated. The Group VIII metal is preferably present in an amount equal to 0.01 to 5.0 wt. % of the finished catalyst. The metal or metal cation having a radius greater than 1.35 angstroms is preferably chosen from Groups IA or IIA and is present in an amount equal to about 0.01 to about 20 wt. % of the finished catalyst. This component of the catalyst is preferably barium, but the use of other metals including rubidium or cesium is also contemplated.

The preferred solid support is alumina having a surface area between 1 and 300 m$^2$/g, an apparent bulk density of between about 0.2 and 1.5 g/cc, and an average pore size greater than 20 angstroms. The metal-containing components are preferably impregnated into solid particles of the solid support by immersion in an aqueous solution followed by drying and calcination at a temperature of from about 500°-600° C. in air. The support may be in the form of spheres, pellets, or extrudates. The total amount of oxidation catalyst present within the dehydrogenation zone is preferably less than 30 wt. % of the total amount of dehydrogenation catalyst and more preferably is between 5 and 15 wt. % of this total amount of dehydrogenation catalyst.

The conditions utilized during the contacting of the reactant streams with the different beds of oxidation catalyst will be set to a large extent by the previously referred to dehydrogenation conditions. The preferred outlet temperature of any bed of oxidation catalyst is the preferred inlet of the immediately downstream bed of dehydrogenation catalyst. The temperature rise across the oxidation catalyst bed should be adjusted to react at least 60 and preferably 85 percent of the hydrogen approaching this catalyst. The liquid hourly space velocity, based on the liquid hydrocarbon charge at standard conditions (15° C.), is preferably between 4 and 20 hr$^{-1}$. It is preferred that substantially all of the oxygen which enters a bed of oxidation catalyst is consumed within that bed of oxidation catalyst and that the effluent stream of any bed of oxidation catalyst contains less than 0.1 mol. % oxygen.

The total moles of oxygen charged to the dehydrogenation zone is preferably more than 35% of the total moles of hydrogen available within the dehydrogenation zone for combustion, and is therefore dependent on the conversion achieved in the dehydrogenation zone. This available hydrogen is the sum of any hydrogen recycled to the dehydrogenation zone and the hydrogen produced in all but the last bed of dehydrogenation catalyst. Preferably, the oxygen charged to the dehydrogenation zone is equal to about 30 to 48 mol. % of the thus-defined available hydrogen. As used herein, the term "substantially all" is intended to indicate a major fraction of the indicated chemical compound(s) has been acted upon in the manner described, with this major fraction preferably being over 90 mol. % and more preferably over 95 mol. %.

What is claimed is:

1. In a process for the catalytic dehydrogenation of a C$_3$-plus dehydrogenatable hydrocarbon wherein a feed stream comprising a feed hydrocarbon is passed into a dehydrogenation zone comprising a first bed of dehydrogenation catalyst maintained at dehydrogenation conditions and a dehydrogenation zone effluent stream comprising hydrogen, a portion of the feed hydrocarbon and a product hydrocarbon is produced, the dehydrogenation zone effluent and an oxygen-containing gas stream are admixed and passed into an oxidation zone comprising a separate bed of selective hydrogen oxidation catalyst maintained at oxidation-promoting conditions, an oxidation zone effluent stream is produced, and the oxidation zone effluent stream is passed into a second bed of dehydrogenation catalyst; the improvement which comprises injecting stream into contact with the dehydrogenation zone effluent stream and using the flow of steam to educe the oxygen-containing gas stream first into admixture with said steam, and thereafter combining said steam and oxygen-containing gas mixture with said dehydrogenation zone effluent and passing the combined gas mixture and dehydrogenation zone effluent into said oxidation zone such that the eduction of the oxygen containing gas by said steam simultaneously mixes said steam and said oxygen containing gas and prevents the addition of said oxygen containing gas into said oxidation zone when said flow of steam is interrupted.

2. The process of claim 1 further characterized in that the steam has a pressure of from 10 to 50 psig.

3. The process of claim 1 further characterized in that the steam educes the oxygen containing gas in a wt. ratio of from 1:1 to 3:1.

4. The process of claim 1 further characterized in that the oxygen-containing gas stream is atmospheric air and all of said atmospheric air is educed into the process by said steam.

5. The process of claim 4 further characterized in that the mixing of the oxygen gas stream and dehydrogenation effluent produces a feed to the oxidation zone having an oxygen concentration of from 1.0 to 2.0 wt. %.

6. The process of claim 1 further characterized in that the feed stream comprises an alkylaromatic hydrocarbon.

7. The process of claim 1 further characterized in that the feed stream comprises ethylbenzene.

8. A process for the catalytic dehydrogenation of ethylbenzene in a multistage reaction zone that includes at least two dehydrogenation zones and at least one oxidation zone which comprises the steps of:

(a) passing a feed stream comprising the ethylbenzene into a first dehydrogenation zone and through a first bed of dehydrogenation catalyst maintained at dehydrogenation conditions and producing a first dehydrogenation zone effluent stream comprising hydrogen, ethylbenzene, and styrene;

(b) passing a stream of dilution steam through an eduction zone to educe an oxygen-containing gas stream into admixture with said dilution steam, said eduction zone educing sufficient oxygen containing gas to supply all of the oxygen requirements of said oxidation zone;

(c) passing the mixture of the oxygen-containing gas stream and the dilution steam into contact with said first dehydrogenation zone effluent to produce an oxidation zone feed stream;

(d) passing the oxidation zone feed stream into a separate bed of hydrogen selective oxidation catalyst and producing an oxidation zone effluent stream;

(e) passing the oxidation zone effluent stream through a second bed of dehydrogenation catalyst maintained at dehydrogenation conditions and producing a second dehydrogenation zone effluent stream which comprises the styrene product; and (f) recovering the styrene product.

9. The process of claim 8 further characterized in that the dilution steam educes atmospheric air and all of the oxygen-containing gas entering said reaction zone is educed therein by dilution steam.

10. The process of claim 9 further characterized in that the steam educes the air in a wt. ratio of from 1:1 to 3:1.

* * * * *